United States Patent [19]
Wirtz

[11] Patent Number: 4,657,003
[45] Date of Patent: Apr. 14, 1987

[54] IMMOBILIZER DEVICE

[75] Inventor: H. Robert Wirtz, Westlake Village, Calif.

[73] Assignee: Cramer Products, Inc., Gardner, Kans.

[21] Appl. No.: 822,052

[22] Filed: Jan. 24, 1986

Related U.S. Application Data

[63] Continuation of Ser. No. 541,789, Oct. 3, 1983, abandoned.

[51] Int. Cl.⁴ .............................................. A61F 5/04
[52] U.S. Cl. .................................. 128/133; 128/89 R
[58] Field of Search ............. 128/89 R, DIG. 20, 133, 128/87 R, 78

[56] References Cited

U.S. PATENT DOCUMENTS 3,212,497 10/1965 Dickenson .................. 128/DIG. 20
3,745,998 7/1973 Rose ..................... 128/89 R
3,762,404 10/1973 Sakita ........................ 128/89 R X Primary Examiner—John D. Yasko
Assistant Examiner—Karen Kaechele
Attorney, Agent, or Firm—Litman, Day & McMahon

[57] ABSTRACT

Immobilizing device for restraining a body portion or limb, comprising an air impervious pliant bag, e.g. of urethane coated nylon fabric, a plurality of lightweight expanded beads, e.g. polystyrene beads, preferably of relatively uniform large size of a diameter greater than 5 mm placed within the bag, and a self-closing valve communicating with the interior of the bag for evacuating air therefrom. The beads are free to be moved and accumulate in those areas where support is most needed. When the interior of the bag is evacuated, the beads are compacted by the collapsing bag and deformed into a rigid construction around the body member for support and restraint thereof. The bag is shaped to completely surround the body member to be supported and releasable strap means preferably are provided to maintain the bag in wrapped position around the body member before and after evacuation. After a period of use, introduction of air into the interior of the bag through the valve again permits freedom of movement of the beads and causes the device to collapse, and the device can then be removed from around the body member by releasing the strap means.

12 Claims, 17 Drawing Figures

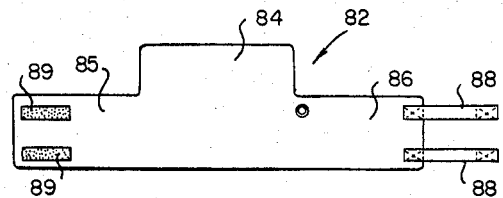
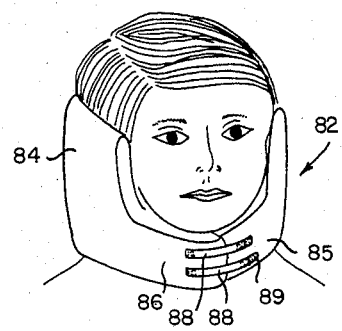
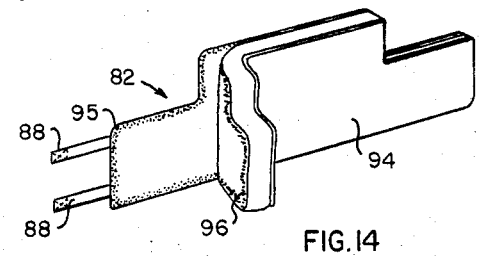
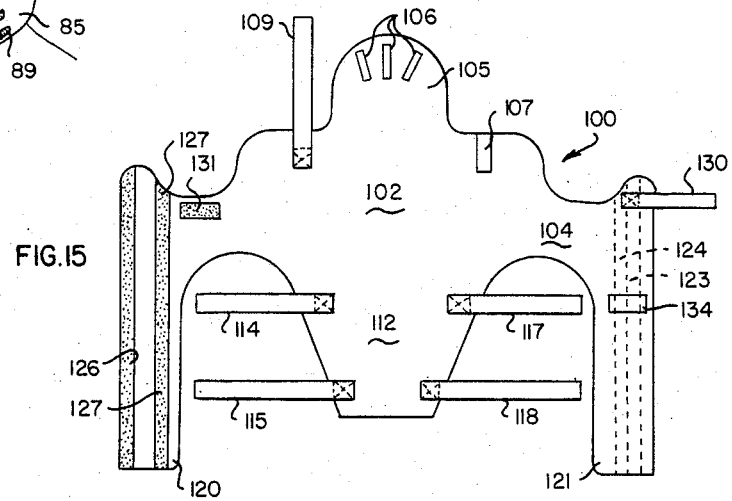
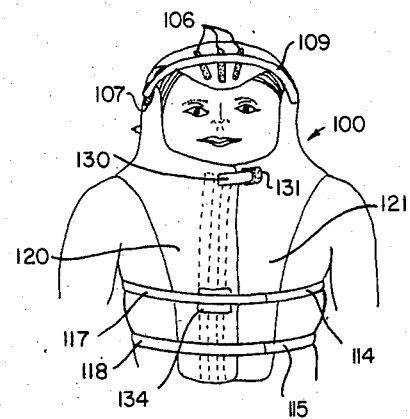
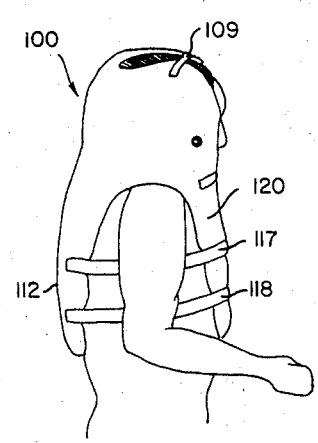

IMMOBILIZER DEVICE

CROSS REFERENCE TO RELATED APPLICATION

The present application is a continuation of Ser. No. 541,789, filed Oct. 3, 1983, now abandoned.

BACKGROUND OF THE INVENTION

This invention relates to devices for immobilizing a portion of the human body, and is particularly concerned with the provision of a device for supporting, restraining and/or immobilizing a portion of the body of a fracture victim or medical patient for reducing or minimizing injury to the individual by reducing freedom of movement prior to full medical procedures, during emergency transport, while conducting radiography, therapy, or surgery, or during recuperation.

Immobilizers and support structures for various body members are highly useful in many situations, particularly in the fields of medicine and therapeutic treatment of human patients. Thus, needs have existed for improved forms of temporary splints and restraining devices for transporting emergency accident victims to places of treatment while immobilizing affected portions of the victim's body to avoid further injury and minimize the effects of injuries already inflicted. Many rigid, semirigid and rigidifiable structures are known and used for these purposes, but all suffer from disadvantages in terms of weight, adaptability to different uses, and ease of employment.

Immobilizer devices should preferably be light in weight and capable of quick and convenient support for the body member being immobilized. Uses include arm or leg immobilizers, for example, for supporting a fractured limb in an immobilized and relatively comfortable position, radiological immobilizers for positioning the body during various radiologic procedures, head and neck immobilizers for use during surgery or in case of head, neck or upper body injury.

Immobilizer devices useful for the purposes noted above should have certain important features or characteristics in addition to light weight. They preferably should be readily conformed to the limb or portion of the body to be supported, regardless of the region at which applied and the attitude of the body structure in that region. The surface of the immobilizer that contacts the individual should snugly follow the body contour, but should not chafe or abrade the user and should also not present a hard surface. Further, the materials used should also be strong and durable, resistant to chemicals such as gasoline and oils encountered during accidents, and able to withstand rough handling prior to use, during application, and while applied.

Illustrative of immobilizer devices which are convertible from a collapsed to a rigidified condition are the devices disclosed in U.S. Pat. Nos. 3,212,497 to Dickinson, 3,745,998 to Rose and 3,762,404 to Sakita. U.S. Pat. No. 3,212,497 was apparently the earliest suggestion of such a collapsible system, and is based upon the use of an outer flexible bag and an inner woven but relatively non-stretchable bag which contains very fine polystyrene crystals. This arrangement undoubtedly proved to be too heavy (the example given is of a 3'×1' bag with 9 lbs. of crystal), and was surely not well adapted for use in emergency situations. U.S. Pat. Nos. 3,745,998 and 3,762,404 were relatively contemporaneous with each other, but the former contains a substantial number of advantageous features relative to the latter. It proposes the usage of a bag of flexible sheet material with internal lightweight polymer beads, the bag in one form being trapezoidal in form and secured by flexible strips upon an arm or other limb. The basic premise is that the beads, although being of formed particles, may be manipulated within the bag to be positioned for best conformity and support, with the detachable straps holding the bag in position, so that the bag may then be evacuated through a non-deformable spring-loaded valve of the type typically used for air-inflated tires. The valves are coupled into the interior of the enclosure by "distributor units" which protrude into the inner volume, so that the valves must be mounted in the side of the structure but the distributor substantially parallel to the surface to be supported. This arrangement is used to avoid the usage of the extra internal envelope of Dickinson U.S. Pat. No. 3,212,497. However, Rose also predicates his system upon the usage of a thin polyurethane film of between 0.002" and 0.014" thick to provide an elastic stretching and shrinking quality, with the beads having a relatively narrow range of bead densities falling between 1.00 and 2.00 lbs/ft$^3$ and outside diameters ranging from 0.015" to 0.125", with a median particle size of 0.050", which is approximately 1.25 mm (the 0.125" diameter being approximately 3 mm). This relationship of small bead sizes to a shrinkable film envelope provides an arrangement in which the outer layer of filler particles may be engaged by the thin film envelope in a "shrinking, interfitting, pebbled embrace". Rose proposes many different forms of usage of this structure, including arm splints, arm slings, neck braces and stretchers, and the latter of which instances he proposes the use of a cushioning material on the surface.

Sakita U.S. Pat. No. 3,762,404 uses a flexible bag, employing an elastic material that may have a rubber mix, but also specifically has a frictional characteristic to prevent movement of the beads. Further to this end he employs internal partitions, and proposes the employment of soft valve constructions of a particular kind. In addition, he suggests that the suitable size range for the internal polymer beads is from 1 mm to 5 mm, using two materially different sizes within this range and with the specific gravities being from about 0.1 to about 0.6, meaning that the density is from about 6 to 36 lbs./ft$^3$. This bag in practice is difficult to apply, difficult to conform to the proper position for the user, and cannot readily be made comfortable because of the inability of the internal beads to shift. In addition, the soft valve inevitably slowly leaks, losing the rigidity of the immobilizer even over a relatively short period of time.

SUMMARY OF THE INVENTION

According to the present invention there is provided a reliable and effective immobilizer device in the form of an uncompartmented impervious lightweight bag or envelope of pliant but non-elastic fabric supported polymer sheet of chemically resistant material and non-frictional characteristics. Expanded polymer or other free-flowing beads in a size range of greater than 5 mm and a bulk density of 0.5 to 2 lbs/ft$^3$ are disposed within the bag. For example beads of 5 mm to 10 mm in diameter, with an average diameter of 7 mm and a bulk density of 1.2 lb/ft$^3$ are used to particular advantage. The pliant but supported envelope permits shifting of the beads for greatest support and comfort of the patient, but does not stretch down or shrink about the filler to provide a pebbled or corrugated effect when a vacuum is drawn. Instead, the relatively large beads compress under the envelope and against each other, to define the rigidified condition. The beads interlock adequately at all regions despite the variations in thickness between the opposite walls, to render the construction rigid around the body member which is constrained. The device cannot be bent, so that the immobilizing effect is enhanced, but at the same time the surface engaging the user is comfortable and the beads can further compress in response to local swelling.

Further features of the immobilizing device of the invention relate to shaping of the devices to fit around particular body regions and to be releasably retained prior to internal evacuation. Thus, for arms and legs, the flexible envelope preferably has a tapered trapezoidal shape of appropriate size. A given size will readily fit around the arm, for example from a position above the elbow down to the wrist, or around the leg from a position above the knee down to the ankle. Closely spaced releasable straps are arranged to encircle the circumference of a limb or other part of the body. The immobilizer device is thus readily adjustable and can encompass body joints at positions above and below a fracture. A larger size device is used for upper leg portions, with a greater number of releasable straps in like dispositions. A neck and head immobilizer is preferably configured as a variable height band having a smaller height joiner region fitting under the chin and releasable straps across the front such that access to vessels and nerves in the chin and front neck region can be gained without removing the device. Also in accordance with the invention, a neck and upper body immobilizer is provided with a configuration that surrounds not only the head, neck and collarbone regions but extends down to the upper back and the upper chest as well. Releasable straps unite the different portions of this unitary structure so as to provide cervical immobilization regardless of the attitude in which the neck and head may be placed.

The strength and physical integrity of the envelope are utilized to advantage in conjunction with other arrangements as well. Although the surface of an immobilizer that faces the patient is not abrasive or frictional in character, an injured limb or other part of the body can be extremely sensitive and for these applications it is advantageous to employ a detachable cushion pad that is peripherally joined in a releasable manner to the interior surface of the immobilizer. The cushion pad may be of thick but soft foam material and of a disposable character. It is also convenient for many applications to utilize the immobilizer as a retention means and insulator for application of an ice bag or heating pad to an injured joint, such as an ankle or knee. Alternatively, however, an externally accessible chamber may be defined by an additional pocket on the interior surface of the immobilizer, and this may be utilized specifically to retain the heating or cooling medium.

A valve, preferably in the form of a spring-loaded valve having a relatively high spring force, is positioned on the flexible envelope in communication with the bag interior through a low profile screen filter that does not protrude into the bag interior. This arrangement permits rapid evacuation of the interior of the envelope by a manually activated or power driven pump. A spring-loaded valve having a substantial internal conduit is used that presents low flow impedance, so that even with a hand pump the immobilizer can be rigidified in a few seconds. Conversely, however, the high spring force of the valve assures a substantially leak free seal, so that the device remains rigid for much more than the anticipated period of use.

BRIEF DESCRIPTION OF THE DRAWINGS

A better understanding of the invention may be had by reference to the following description, taken in conjunction with the accompanying drawings, in which:

FIG. 12 is a plan view of a neck brace immobilizer device;

FIG. 13 is a simplified perspective view of the device of FIG. 12 as installed;

FIG. 14 is a perspective view of a modified immobilizer in accordance with the invention;

FIG. 15 is a plan view of a different form of cervical immobilizer device;

FIG. 16 is a front view of the device of FIG. 15, as configured when in use; and FIG. 17 is a side view of the device of FIGS. 15 and 16, as configured when it is in use.

DETAILED DESCRIPTION OF THE INVENTION

Figure 1:
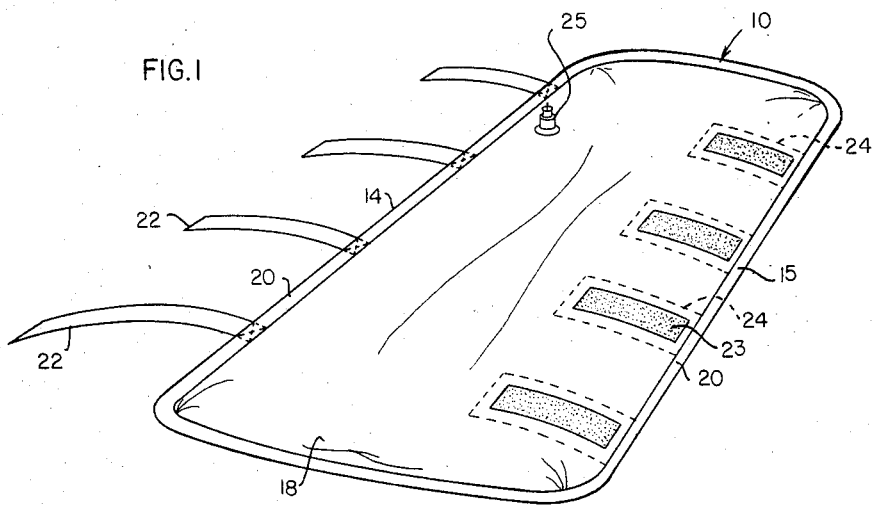
FIG. 1 is a perspective view of the inner side of an immobilizer device of the present invention shown in its collapsed form.
Figure 2:
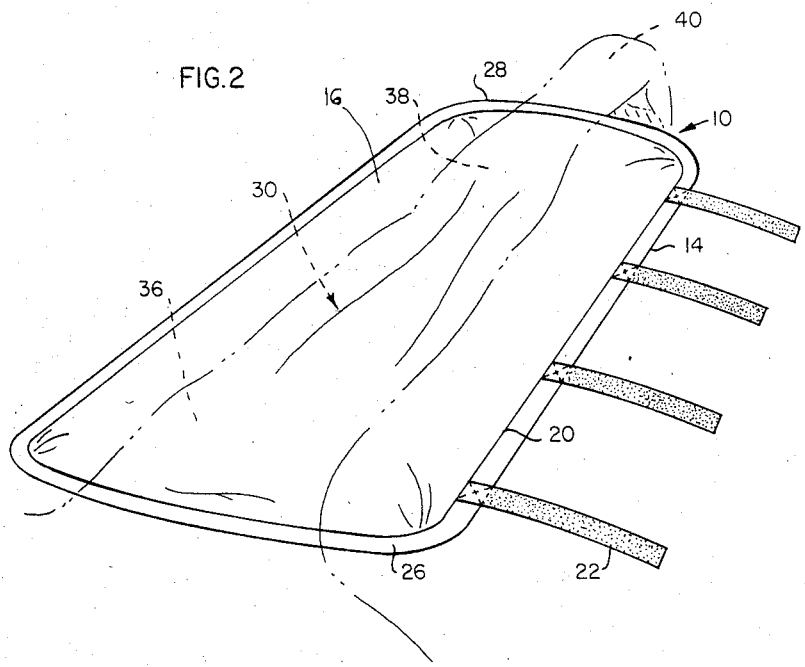
FIG. 2 is a perspective view of the outer side of the immobilizer device of FIG. 1.
Figure 3:
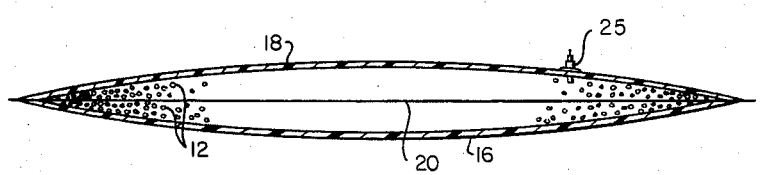
FIG. 3 is a simplified longitudinal section through the immobilizer device of FIGS. 1 and 2.
Figure 4:
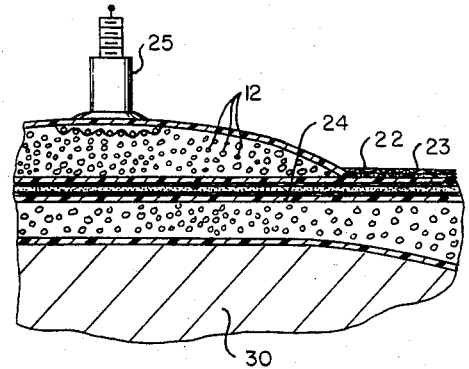
FIG. 4 is a fragmentary cross-sectional view showing the immobilizer of FIGS. 1-3 wrapped in secure position relative to a patient's limb prior to rigidification.
Figure 5:
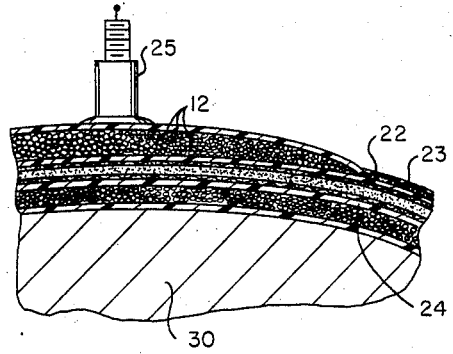
FIG. 5 is a fragmentary cross-sectional view similar to FIG. 4, showing the same immobilizer applied to the patient's limb and secured in its applied condition and rigidified in its support mode.

Referring to FIGS. 1-5, there is shown one form of the immobilizer device of the invention comprising an airtight envelope or bag 10 of air impervious material containing a charge of deformable plastic beads 12 (FIGS. 3-5 only). The bag 10 has tapered sides longitudinally of the bag, as indicated at 14 and 15, so that the bag has a generally trapezoidal shape and conforms to the changing dimension of a limb about which it is applied.

The bag is formed of a inner or front sheet 16 and an outer or back sheet 18 of pliant but non-shrinkable synthetic plastic material cut into correspondingly shaped sheets and sealed together around their mating peripheries as by heat sealing, to form a closed pressure-tight envelope with a closed peripheral seal region or edge 20. The sealed edge 20 provides a peripheral area to which various members may be attached. The material forming the front and back sides 16 and 18 of the bag can be any supported material having good durability and airtightness and resistance to chemicals (including ozone), including plastics such as nylon, polyvinyl chloride, polyethylene, polypropylene, tetrafluoroethylene resins, acrylic esters and polyurethane. Preferably, nylon fabric having a urethane coating is employed, to present a smooth exterior surface resistant to abrasion and a low friction interior surface. This combination does not deteriorate under attack by corrosive or strong chemicals, such as gasoline, oils and greases that come in contact with an accident victim, nor does it age or degrade appreciably in response to sunlight or the presence of ozone. In addition, the material is pliant and readily shapable, so that smooth filler material in the interior can be adjusted within the low friction surface but is rigid within its own plane due to the presence of the supporting fabric. Consequently, it is not flexible in this dimension, and does not shrink tightly about a small interior object when the inside of the envelope is evacuated.

A plurality of straps 22, shown as four in number, are secured to the peripheral seam 20 region along one tapered edge 14 of the bag 10 as by sewing. The straps 22 are disposed closely enough together to enable initial attachment of the immobilizer without any looseness at the ends or in a midregion. For an arm or ankle immobilizer, which is approximately 24" long, four equally spaced straps 22 are employed. Such straps are preferably in the form of "Velcro" fabric straps 22 which extend beyond the periphery of the bag to protrude from one edge 14 of the envelope. The straps 22 cooperate with Velcro fabric patches 23 secured to the back or inner sheet 18 of the bag 10 and extending inwardly from the opposite tapered edge 15 of the envelope, as best shown in FIG. 1. "Velcro" is the registered trademark of Smalley and Bates, Inc., identifying a disengageable securing material comprising open loop pile fabric on one element cooperating with tiny protruding plastic hooks on the other element, which hooks are deformable for engagement with the loop pile, and individually deformable for peeling disengagement of one element from the other. Although the fabric patches 23 may be sewed to the back sheet 18, the hermetic seal is maintained by thereafter attaching backing strips 24 to the opposite side of the back or outer sheet 18, and joining these backing strips 24 to the interior side of the back sheet 18 by heat sealing or other conventional means that maintains the airtight integrity of the sheet 18.

The interior of the bag or envelope 10 is partially filled loosely in the collapsed mode shown in FIGS. 1 and 2 with a large number of small lightweight granules or beads 12 preferably formed of expanded plastic materials such as polystyrene or polyvinyl chloride. Such beads are of high mechanical strength, low specific gravity and elastic deformability. The beads have multiple closed cells and are formed from foamed synthetic resin, while preferably ranging in size from as low as 5 mm to about 10 mm, or greater in this example. In practice, any given commercial product has a range of sizes representing variations from a target size, so that an average size of 7 mm is typical. In addition, the beads are of low density, in the range of 0.5 to 2.0 lbs/ft$^3$ with 1.2 lbs/ft$^3$ being typical. The figure given is for the bulk density of a given volume of the beads packed together without compression. Such beads are elastically deformable within a range, but may fracture if further stressed. This, however, does not materially affect the performance of the immobilizer. The larger size beads and elastic characteristic are utilized in conjunction with the non-shrinkable envelope as described hereafter. The beads are freely and loosely packed in the envelope in the collapsed mode, as shown in FIG. 4, permitting free rolling contact between the beads and facile manipulation of the immobilizer bag to conform to the shape of a body member. Such larger diameter beads are more pliable than the smaller diameter beads of from 1 mm to 5 mm diameter, and are less prone to breaking down under flexing and disintegrating to form a powder.

A valve 25 is connected to the back or outer sheet 18 of the immobilizer bag 10, which functions to evacuate the interior of the bag by connecting a source of negative pressure to the valve. Such valve 25 preferably is a self-closing valve in the form of a rigid spring-loaded needle valve to which can be connected a vacuum pump such as a manual or powered pump to evacuate air or gas inside the envelope while the plastic beads remain packed in place and without withdrawing any of such beads. It is convenient to employ a hand held reciprocating piston pump (not shown) with a fitting at each end for alternative attachment to the valve 25. Thus one fitting can be coupled to the valve for evacuating air to collapse the bag, and then after use of the immobilizer the same pump can be coupled, via the other fitting, to quickly fill the bag and enable removal of the immobilizer.

In utilizing the immobilizer device of the invention for supporting a patient's arm, including the portion above the elbow, as seen in FIG. 2, the front side 16 of the immobilizer device of the invention is positioned beneath the patient's arm 30 with the upper edge 26 of the bag 10 positioned adjacent the upper arm 36 above the elbow, and with the lower edge 28 of the bag positioned adjacent the wrist 40. The envelope 10 is then wrapped firmly around both sides of the patient's arm 30, and secured in this retained position by attaching the Velcro straps 22 to the Velcro patches 23 on the outside surface 18 of the bag 10. It will be noted that the upper large portion of the bag 10 and the lower smaller portion thereof are such that the bag entirely surrounds the upper muscular portion 36 of arm 30 as well as the smaller forearm portion 38, with some overlapping of the opposite edge portions of the bag, when the immobilizer is in the completely wrapped position shown in FIGS. 4 and 5.

In the collapsed mode of the bag 10 as seen in FIG. 4, because the inside surface of the urethane coated flexible nylon bag is very smooth and the beads are slippery and light weight, the beads 12 readily distribute themselves to a degree. The person applying the immobilizer can also shift and pack the beads into those areas where support is required, and eliminate any points of discomfort that may be felt. Further, particularly since there are no compartments, supports or other obstructions in the interior of the bag, this permits maximum freedom of the beads to pack together where support is best needed. Even where the cross-section of the envelope may be thinnest there will be an adequate number of beads available to insure rigidity.

When negative pressure is applied to the interior of the bag as by applying a few drafts on a suitable pump attached to the valve 25, the envelope or bag is quickly evacuated to form a rigid pack by contact of the beads with each other, and by closure of the sides of the bag on the beads, even though the sides do not stretch the packed beads, as seen in FIG. 5. This results in a rigid unit which covers the arm above and below the elbow and maintains the arm between the elbow and the wrist in a fixed position. The immobilizer structure can be placed and maintained in its rigidified position as shown in FIG. 5 by employing an internal pressure below half an atmosphere, although at lower pressures the immobilizer is better able to maintain its form. The vacuum in the immobilizer can be maintained within the interior of the immobilizer for a substantial period, e.g. for up to seven days or more. In the rigidified position of the immobilizer as seen in FIG. 5, the arm is anchored in position, and articulating movement of the arm from the elbow is effectively inhibited.

When the immobilizer device is no longer required, the device can be quickly and conveniently collapsed by introducing air through valve 25 into the interior of the bag, which causes the interior surfaces of the bag to move away from the beads, and permitting the beads to unpack and again move freely within the bag so that the immobilizer is now again flexible. The Velcro straps 22 are then turned or peeled away from the complementary Velcro patches 23, causing the bag to unroll from opposite sides of the arm to its position shown in FIGS. 1 and 2, whereupon the immobilizer can then be removed.

Figure 6:
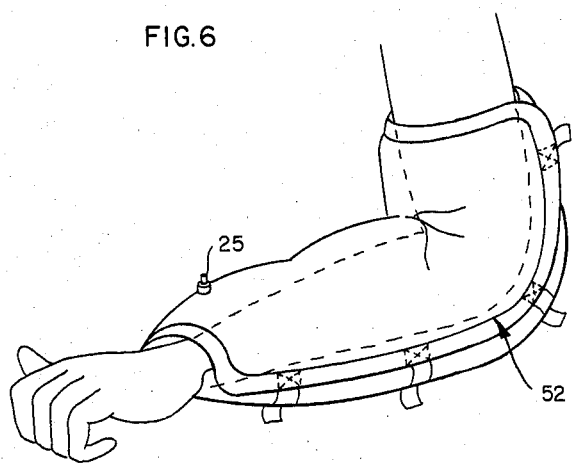
FIG. 6 is a perspective view showing the immobilizer of FIGS. 1-5 shown secured in its applied and rigidified support condition for supporting a patient's arm above and below the elbow.

In different applications of the immobilizer shown in FIGS. 1-5, the device 52 can be rigidified about a bent elbow as shown in FIG. 6, as well as a straight arm as shown in FIGS. 1 and 2. The same size device can be wrapped about the lower portion of a leg 42 and extending above the knee 43 for supporting and immobilizing the leg 42 below the knee. For larger diameter applications, such as above knee or in the thigh region, the same shape is employed but the size is larger, e.g. $3\frac{1}{2}'$ in length, and a greater number of straps may be used.

Figure 7:
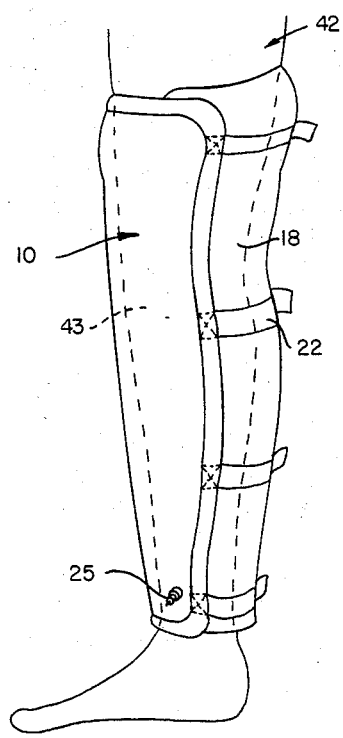
FIG. 7 is an elevational view showing the immobilizer of FIGS. 1-5 secured in its applied condition and rigidified in its support mode for supporting the leg of a patient above and below the knee.
Figure 8:
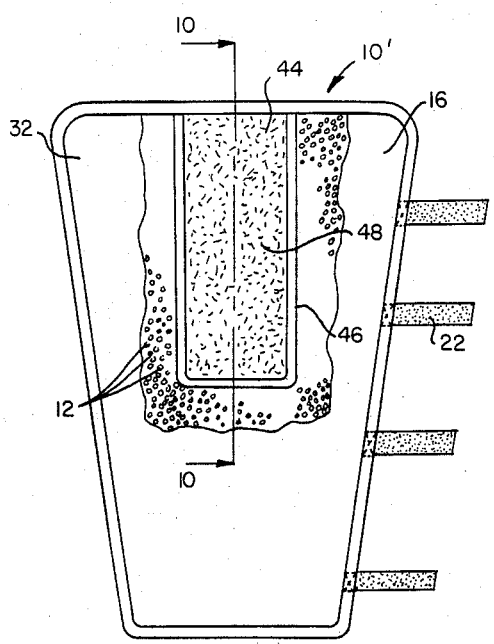
FIG. 8 is a modification of the immobilizer of FIGS. 1-5, and partially broken away to show a compartment for a therapeutic material such as ice.
Figure 9:
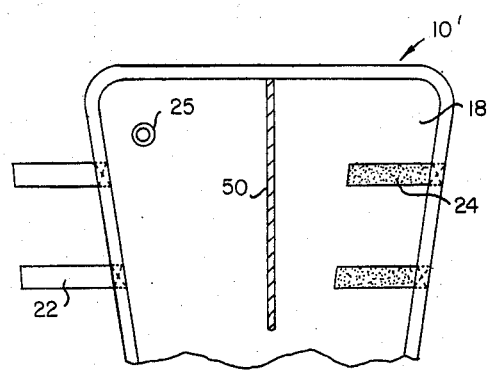
FIG. 9 is a partial backside view of the immobilizer of FIG. 8.
Figure 10:
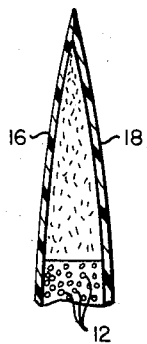
FIG. 10 is a partial section taken on line 10—10 of the immobilizer of FIGS. 8 and 9.

According to a modification of the immobilizer device of the invention, as shown in FIGS. 8-10, a separate compartment 44 is provided along a portion of the length of the bag 10′, e.g. about one-half of the length of the bag from the wider portion 32 thereof, and defining a minor portion of the interior of the bag. The compartment 44 can be formed by connecting a U-shaped piece of flexible fabric such as urethane coated nylon, indicated at 46, to opposite sides 16 and 18 of the bag. A therapeutic material such as chopped ice indicated at 48 can be placed in the compartment 44 by means of a slide fastener 50 in the outer side 18 of the bag 10′, permitting access to the interior of compartment 44. It will be seen that when the immobilizer 10′ of FIG. 8 is wrapped around opposite sides of an arm or leg as shown in FIGS. 6 and 7, the ice-containing compartment 44 will be positioned around the elbow or knee. Thus when the immobilizer device is in the rigidified mode around the arm or leg it is used not only to support the limb in a fixed inarticulate position, but the ice in compartment 44 functions as a therapeutic agent for the joint. Thus this device may be used as for example for use by a pitcher for treatment of a sore or stiff elbow after a baseball game. It will be seen that the presence of the compartment 44 will not interfere with freedom of movement of the beads 12 throughout the entire interior of the bag outside the compartment 44, so as to function efficiently when the interior of the bag is placed under vacuum, to pack together in all areas of the bag interior outside the compartment 44, for suitable support of the arm. In effect, the interior of the bag containing the beads is the entire volume of the bag externally of the compartment 44, and such volume, as in the case of the example of FIGS. 1-4, also is free of any walls or obstructions which would interfere with freedom of movement of the beads therein.

Figure 11:
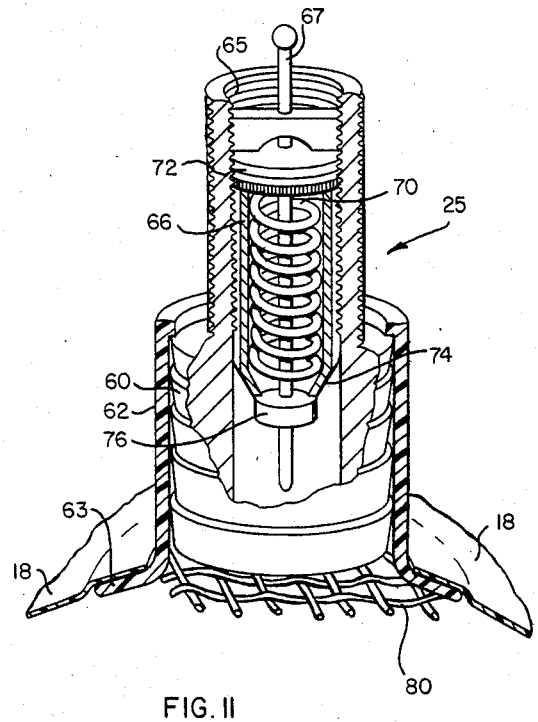
FIG. 11 is a perspective view, partially broken away, of a spring-loaded valve and filter arrangement used in devices in accordance with the invention.

A particularly advantageous form of construction for the valve 25 is depicted in FIG. 11, to which reference is now made. A valve body 60 is seated within an elastomeric sleeve 62 which has a substantially flat base 63 fitting inside an opening of the bag, and bonded by heat seal or other means to the inside of the bag. Tapered portions on the outside of the body 60 enable the body to be set firmly into the elastomeric sleeve 62 without leakage occurring. The threaded interior portion 65 of the valve body 60 permits threaded insertion of a valve assembly 66, the stem 67 of which is urged upwardly by a compression spring 70 acting against an upper member 72 which receives the central stem. The lower edge of a tapered portion 74 of the body is engaged by a valve seat 76 disposed about the central stem 67, when the spring is in its normal position biasing the stem 67 to its upper limit. However, when the stem 67 is depressed as by attachment of a fitting to draw a vacuum or inject air, a wide opening is presented between the engaging surfaces 74, 76, to permit the passage of air in either direction. This internal mechanism is generally known as a Schrader valve and is a type of device well known in the tire industry. However, applicant prefers to utilize a heavy duty spring 70 which substantially increases the spring force that must be overcome to open the valve, but at the same time insures against leakage, particularly under internal vacuum conditions. Inasmuch as the valve body 60 does not extend below the sleeve 62, and inasmuch as the valve 25 is utilized on a side away from the patient to which the immobilizer is applied, this arrangement is far superior to the soft valves and internal distributors heretofore used. As previously noted, a vacuum can be maintained in a bag for seven days or more.

The internal bead material does not tend to escape into the valve 25, because a low profile screen 80 having openings sufficiently small to prevent passage of internal foam particles, is disposed between the bag interior and the valve body 60, and molded or attached against the inside surface of the bag wall 18. Consequently, there is no protuberance of substantial magnitude internally relative to the bag, and there is no tendency to create a pressure point or any other discomfort for the user.

It will be understood that the invention device can be employed for supporting and immobilizing other portions and members of the body. Thus, it can be employed as a neck collar and can be employed around the back in a position below the waist and up to and above the shoulders.

A neck brace arrangement in accordance with the invention is illustrated in FIGS. 12 and 13. The neck brace 82 comprises a substantially rectangular center portion 84 which, as seen in FIG. 13, is intended to wrap around the back of the head and the sides of the head of a user. The neck brace includes end tabs 85, 86 that are integrally connected to and extend from the central region 84. Velcro straps 88 attached to one end tab matingly engage with complementary Velcro patches 89 secured to the other of the end tabs 85. When placed in position on a user, as seen in FIG. 13, the back and sides of the head are fully supported, and the interior foam may be adjusted to match the curvature and the various concavities in the neck and head region. The end tabs 85, 86 meet together under the chin, and are secured across the front of the neck by attachment of the complementary Velcro portions 88, 89. However, unlike the conventional neck brace, which is engaged at the back of the head, this arrangement provides access to the throat and jaw regions, to examine whether there is any trauma to or occlusion of vessels or parts of the nervous system. When the neck brace 82 is rigidified by evacuation, the straps 88 may be detached, and the medically important regions about the neck may be examined for possible problems.

The arrangement of FIG. 14 depicts a neck brace but illustrates a modification that may be employed with all immobilizers in accordance with the invention. As seen in FIG. 14, the inner surface of the neck brace 82, that is the surface that is to engage the skin of the wearer, is covered with a sheet of cushioning material 94 such as $\frac{1}{4}$" to $\frac{3}{4}$" soft plastic foam. In addition to conforming the disposition of the beads so as to conform to the wearer in the region to which applied, the soft cushion material 94 enables discomfort to be further reduced. It is preferred, as shown in FIG. 14, to employ complementary Velcro hook and fabric strips 95, 96 around all or a substantial part of the periphery of the neck brace 82 and the cushion material 94. Consequently, after use for a period of time, the sheet material 94 may be removed and replaced with a new disposable cushioning material.

FIGS. 15, 16 and 17 depict a different form of immobilizer, this intended for use in immobilizing not only the head and neck but a substantial portion of the upper body as well. This immobilizer 100 is integral and therefore has complete intercommunication between the different principal parts, but has a more complex peripheral shape. A central region 102 is substantially rectangular in form, and provides a neck brace which, together with immediately adjacent side regions 104 can be seen to define a neck brace comparable to the arrangement of FIGS. 12 and 13. That is, the back and sides of the head are engaged, while the side edges meet under the chin of the user. However, for complete engagement of the head an upstanding crown 105 extends so that it can be bent down over the top of the user's head. The crown 105 includes Velcro loop patches 106 which are on the upper surface of the crown when it is bent down over the user's head. A separate Velcro loop patch 107 is disposed adjacent one edge of the central region 102, adjacent the crown 105 on one side, while a Velcro strap 109 is disposed on the opposite side of the crown 105. Thus, as seen in FIGS. 16 and 17, when the crown 105 is conformed to the top of the head of the user, the strap 109 engages the loop patches 106, 107 to provide initial immobilization, which is made secure when an internal vacuum is drawn within the immobilizer 100.

Below the central region 102 a back support region 112 extends below the neck of the wearer. Pairs of engageable straps 114, 115 and 117, 118 mounted along opposite sides of this back support region 112 are disposed to be joinable after passing about the body of the wearer. Velcro hook and loop material is preferred for these straps 114, 115 and 117, 118. The extreme ends of the central region 102 terminate in side wings 120, 121 which abut across the upper chest of the wearer under the chin. One of the wings 121 is provided with vertical Velcro hook strips 123, 124 disposed vertically along the wing 121, to engage vertically disposed Velcro loop strips 126, 127 disposed vertically on the opposite wing 120, when the wing 121 is overlapped on top of the wing 120. A Velcro loop strap 130 extending laterally from the wing 121 then engages a Velcro hook patch 131 in the region of the chin of the wearer. A Velcro fabric patch 134 is also provided on the outside of the wing 121, to provide engagement to the associated straps 114, 117 which go around the body.

Thus, as seen particularly in FIGS. 16 and 17, potential or actual cervical damage to a patient is counteracted by fully immobilizing the patient, utilizing the shoulders, sternum, cervical and thoracic spine, and anterior rib cage, to achieve total immobilization. When the immobilizer 102 is rigidified, the apex of the head is tied into all three structures via the support on the sides and the back of the head, and the interconnected support from the crown 105. The overlapping wings 120, 121 meeting under the chin extend down across the upper chest region and not only support the anterior neck and chin region, but derive base support from the back as well as the sternum, because the interconnecting loop pairs 114, 117 tie to the back region and also to the wings 120, 121 at the front.

This arrangement provides secure engagement and immobilization of the entire upper body above the chest region, assuring in these extremely sensitive cases that no dislocation of collarbone, neck or upper vertebrae will occur.

Immobilizer devices of the invention can be used as a cast and X-ray pictures can be taken through the device, as for example when setting bones following a fracture. The device can be used over dressings and as a positioning aid and in surgery. The device also can be used in the form of a "papoose board" for cradling and immobilizing young children, e.g. up to three to four years old.

From the foregoing, it is seen that the invention provides an improved immobilizer device in the form of a pliant but non-shrinking bag or envelope having lightweight deformable plastic hollow spheres or beads therein, the bag being of a shape which can be readily placed around a portion of the body or limb and secured thereto by releasable retaining means. The beads, being of relatively large size and readily shiftable internally, withstand the forces of compression by compacting as the bag is drawn down. However, secure immobilization is assured by deformation of the beads rather than flexing of the envelope and further if the patient is subject to tissue edema or other swelling the beads will responsively yield to prevent local damage or discomfort.

Since various changes and modifications of the invention will occur to and changes be made readily by those skilled in the art without department from the invention concept, the invention is not to be taken as limited except by the scope of the appended claims.

What is claimed is:

1. A vacuum immobilizer device being reversibly convertible from a collapsed and easily manipulated condition wherein said device may be roughly conformed to an object to be supported to a rigidified condition wherein said device maintains a substantially firm shape and is suitable for immobilizing the object to be supported, said device comprising:
  (a) an air impervious lightweight pliant envelope having an interior and an exterior surface;
  (b) a plurality of lightweight expanded polymer beads having exterior surfaces and diameters of generally greater than five millimeters, loosely filling a portion of the interior volume of said envelope;
  (c) said envelope substantially being open internally so as to permit movement of said beads throughout said envelope and to permit said beads to accumulate in the areas of said envelope where support is required; said envelope interior surface being relatively low friction relative to said beads and said bead exterior surfaces being relatively slippery with respect to said envelope interior surface; and said envelope including a fabric support and being generally non-elastic;
  (d) whereby when a vacuum is applied to said envelope interior so as to produce a partial vacuum within said envelope, said beads are slippery with respect to said envelope interior and said envelope fabric support tends to support said envelope and limit said envelope from being drawn tightly between adjacent beads such that said beads are generally movable within said envelope to allow easier adjustment of the device to conform to the object to be supported and to provide better patient comfort;
  (e) detachable securement means coupled to said envelope for securing said envelope about the object to be supported; and
  (f) valve means mounted on said envelope exterior surface and communicating with said envelope interior, whereby a vacuum source can be connected to said valve for reducing the air pressure inside said envelope, compressing said beads into contact with each other and pulling said envelope into contact with said beads and whereby air can be readmitted through said valve into said envelope interior to convert said device from said rigidified condition to said collapsed condition.

2. The device of claim 1, said polymer beads being expanded hollow polystyrene beads having a bulk density of 0.5 to 2.0 lbs/ft$^3$ and an average size of approximately 7 mm.

3. The device of claim 1, said envelope comprised of sheets of flexible urethane coated nylon fabric joined together adjacent the periphery with a hermetic seal, the securement means being coupled to the envelope and comprising elongated pieces of complementary locking but detachable material secured to the envelope adjacent edges of the envelope that are opposed and closely spaced apart when the device is conformed about an object.

4. The device of claim 3, said envelope including seal means adjacent the periphery, said retaining means comprising fabric strips secured to the envelope along one edge thereof outside the seal means and complementary patches secured along the opposite edge of the envelope for mating engagement between the elements, said patches including backing means interior to the sheet for maintaining the hermetic seal.

5. The device of claim 1, said envelope having tapered sides longitudinally of said envelope, and said envelope having a substantially trapezoidal shape and the securement means being disposed transverse to the tapered sides.

6. The device of claim 1, said envelope defining a neck brace having a principal portion of constant height for fitting around the back and sides of a head and end tabs of lesser height for meeting under the chin of a head, the end tabs having one edge collinear with one edge of the principal portion, and the securement means being coupled to the end tabs and substantially parallel to the collinear edge.

7. The device of claim 1 where the object is a human requiring upper body restraint, said envelope defining an integral neck and upper body immobilizer comprising a central region defining a neck and head support band for the back and sides of the neck and head, a head crown support region extending symmetrically upwardly from a part of the length of the central region and including detechable means for engaging the head crown support region to the neck and head support band, a back support region extending downwardly from the central region and including detachable securement means engageable to each other above the body of the wearer, and a pair of front support wings, each coupled to a differenet end of the central region and extending downwardly therefrom, for engaging the upper front part of the body of the wearer, and including detachable securement means for coupling said wings together in overlapping relation.

8. In an immobilizer device of the type being reversibly convertible by application of an internal vacuum between a collapsed condition in which said device can be manipulated to conform to an object to be supported and a rigidified condition in which said device retains a generally firm shape immobilizing a part of the body of a patient; said device including:
  (a) an airtight pliant bag having an interior surface and an exterior surface;
  (b) a plurality of expanded polymer beads filling a portion of an interior volume of said bag;
  (c) valve means mounted on said bag exterior surface and communicating with the interior thereof for enabling drawing of at least partial vacuum within said bag to generally rigidify said device when said device is about the object to be supported in a desired position;
the improvement comprising:
  (d) substantially each of said beads having a diameter between five and ten millimeters and said beads being slippery relative to said bag interior;
  (e) said bag being substantially free of internal obstructions;
  (f) said bag including a relatively low friction interior surface permitting freedom of flow of said beads in said envelope when said bag is manipulated to conform to and about an object to be supported in a desired position, and permitting said beads to pack together in areas of said bag where support is required;
  (g) said bag being constructed of a fabric supported generally non-elastic polymer sheet, such that said sheet resists being drawn between beads when a vacuum is drawn within said bag;
  (h) whereby when at least a partial vacuum is drawn within said bag, said bag becomes in general rigid, however, said beads are generally manipulative within said bag so as to allow adjustment of said device to better conform to the object to be supported or to provide better patient comfort.

9. The device according to claim 8 including:
(a) retaining means attached to said bag for securing said bag around the object to be supported.

10. The device of claim 9, said bag having tapered sides longitudinally thereof, and said bag having a substantially trapezoidal shape, and wherein said retaining means comprise fabric straps secured to the bag along one side thereof and cooperating fabric patches secured to the backside of the bag along the opposite edge thereof for mating enagement by the fabric straps, said fabric straps comprising open loop pile fabric cooiperating with minute protruding plastic hooks on said patches which are deformable for engagement with the loop pile of said straps and deformable for peeling diesengagement of said straps from said patches.

11. The device of claim 9, including an enclosed compartment within the interior of said envelope and defining a minor portion of the interior volume of said compartment, said beads having freedom of movement in the entire interior volume of said bag externally of said compartment.

12. The device of claim 9, and further including sheet cushioning means coextensive with the side of the device engaging the user, and detachable engagement means mounted about the periphery of both the bag and the cushioning means.

* * * * *